United States Patent [19]
Barrett

[11] 3,990,119
[45] Nov. 9, 1976

[54] SCROTUM SAC

[76] Inventor: Irene J. Barrett, 203 Pidgeon Hill Road, Huntington Station, N.Y. 11746

[22] Filed: Apr. 29, 1975

[21] Appl. No.: 572,929

[52] U.S. Cl. ............................................. 4/1; 4/110
[51] Int. Cl.² ...................................... A47K 17/00
[58] Field of Search ................. 4/112, 111, 110, 6, 4/7, 185 R, 185 HB, 185 S, 1; 128/295

[56] References Cited
UNITED STATES PATENTS

| | | | |
|---|---|---|---|
| 1,499,161 | 6/1924 | Farnsworth | 4/112 |
| 1,631,656 | 6/1927 | Sweeney | 4/112 |
| 2,801,424 | 8/1957 | Mercer | 128/295 X |
| 2,840,826 | 7/1958 | Ebbesen et al. | 4/1 |
| 3,025,531 | 3/1962 | Baker | 4/112 |
| 3,295,146 | 1/1967 | Martin et al. | 4/185 HB |
| 3,588,921 | 6/1971 | Nagel | 4/1 |

*Primary Examiner*—Henry K. Artis
*Attorney, Agent, or Firm*—Kane, Dalsimer, Kane, Sullivan and Kurucz

[57] ABSTRACT

A scrotum sac adapted to be removably mounted on a bed pan and the like. The sac includes a central support cup adapted to receive and protect the scrotum and male organs therein. A fastener structure extends from the cup and is adapted for removably mounting the sac on a bed pan.

8 Claims, 3 Drawing Figures

SCROTUM SAC

BACKGROUND OF THE INVENTION

In dealing with male patients, especially after surgery, it is important that the patient be kept as clean as possible after the use of a bed pan. Especially in instances after surgery of the male organs, the danger of infection is always present and when the male patient requires the use of a bed pan there is often the occurrence of soiling of the male organs. The ultimate result can often be infection which is extremely dangerous. At present, in order to avoid this problem when bed pans are employed, the nurses are required to clean the male patients particularly after bowel movements.

It can be readily ascertained that this can be an extremely undesirable occurrence and can often adversely affect the male patient's pride.

Furthermore, the need of the nurses to clean the male patients after bowel movements is a time-consuming job and adds to the expense both in the hospital and in nursing homes. Particularly in nursing homes, the elimination of this nursing service can save endless dollars and time when help is at a premium.

There is no question that the need exists for a device to provide time, save money, help prevent infection and provide more dignity to male patients when dealing with natural functions of the body.

SUMMARY OF THE INVENTION

With the above background in mind, it is a primary objective of the present invention to provide a scrotum sac which is adapted to be mounted to a bed pan or similar device and which will provide for protection and support of the scrotum and male organs while he is utilizing a bed pan. The resultant device alleviates the necessity of nursing time to clean the patient after natural functions such as bowel movements while still helping to eliminate infection in instances such as post surgery circumstances and which provides more dignity to male patients who are situated in very trying circumstances.

In summary, the device is a scrotum sac adapted to be removably mounted on a bed pan and the like. The sac includes a central support cup adapted to receive and protect the scrotum and male organs therein. Fastening means extends from the cup for removably mounting the sac on a bed pan.

With the above objectives, among others, in mind, reference is had to the attached drawing.

DESCRIPTION OF THE PREFERRED EMBODIMENT

Figure 2:
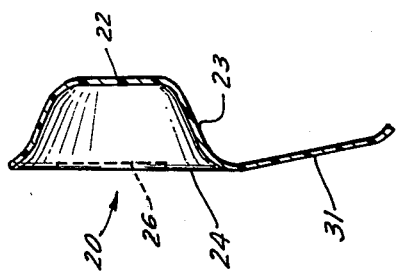
FIG. 2 is a sectional end view thereof taken along the plane of line 2—2 of FIG. 1.
Figure 1:
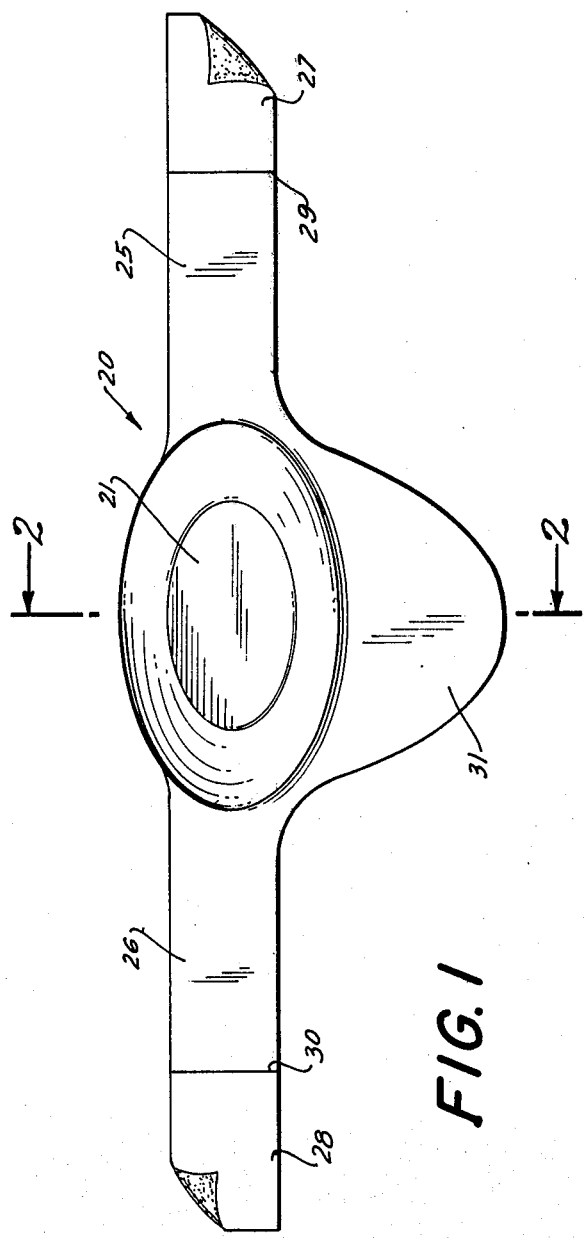
FIG. 1 is a top plan view of the scrotum sac of the invention.

The scrotum sac 20 includes a central cup-shaped member 21 having a bottom wall 22 and a sloping side wall 23 terminating in an open top 24. Extending laterally from the cup-shaped central portion 21 are a pair of diametrically opposed arms 25 and 26 which terminate in free end portions 27 and 28 respectively.

A bend line 29 separates end portion 27 from the remainder of arm 25 and similarly a bend line 30 separates end portion 28 from the remainder of arm 26.

Figure 3:
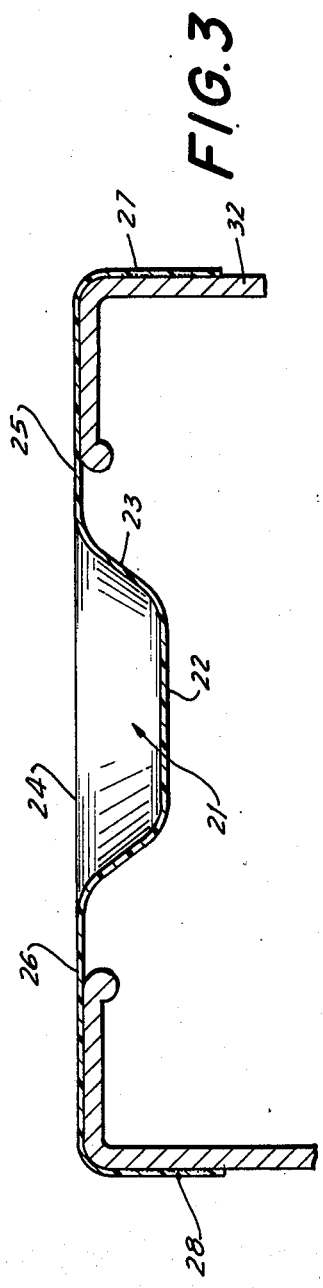
FIG. 3 is a sectional front elevation view thereof taken along the plane of line 3—3 of FIG. 1 and showing the scrotum sac mounted on a bed pan.

A flap or flange 31 integrally formed with cup 21 and arms 25 and 26 extends downwardly from the rim of cup 21 along the rim portion of the cup between one side of each of the pair of arms 26. The flap 31 assists in positioning the male genitals in the proper location within protective cup 21 and also assists in mounting the scrotum sac 20 on a bed pan 32 which is depicted in FIG. 3.

In use, scrotum sac 20 is positioned over the top opening of bed pan 32 and properly aligned with the assistance of flap 31. Thereafter, the ends 27 and 28 containing adhesive on the inner surface are bent downwardly into engagement with the side walls of the bed pan 32 as depicted in FIG. 3. The adhesive of interengagement serves to retain the scrotum sac 20 in fixed position ready to receive the scrotum and genitals of the male patient. In this manner, the patient is protected from contact and contamination with waste materials accumulating in the bed pan. Consequently, it is not necessary for the nurse to clean the patient after the bed pan has been utilized thus saving nursing time and helping to maintain the pride of the patient.

Scrotum sac 20 can then be easily removed, if desired, by removing the adhesive end portions 27 and 28 from the sides of the bed pan and detaching the scrotum sac 20 from bed pan 32. It can then be disposed of.

The scrotum sac 20 can be constructed of any convenient material with the cost factor as well as other factors in mind. For example, it can be a conventional plastic material or a common type of rubber material or a common type of metal material.

The adhesive employed can be any conventional type of adhesive such as an epoxy. Naturally, alternative fastening means can be employed such as snaps or buttons or clips. It is also contemplated that the cup portion can take a different configuration such as square or rectangular in addition to the circular shape shown. In any event, with the general configuration of the present structure, it is possible to use the device on a bed pan with a patient in one of many different positions.

It is also contemplated that among the embodiments of the present invention the scrotum sac 20 can be formed as an integral part of bed pan 32. This can be accomplished in a number of conventional fashions such as by molding the bed pan and scrotum sac combination or by permanently fastening the scrotum sac to the bed pan in some other well known convenient manner.

Thus, the several aforenoted objects and advantages are most effectively attained. Although several somewhat preferred embodiments have been disclosed and described in detail herein, it should be understood that this invention is in no sense limited thereby and its scope is to be determined by that of the appended claims.

What is claimed is:

1. A scrotum sac adapted to be removably mounted on a bed pan and the like comprising; a central support cup having a receptacle configuration which generally conforms to the scrotum and male organs, and fastening means extending from the cup for removably mounting the scrotum sac on a bed pan with the central support cup in position to surround and protect the scrotum and male organs from contaminating waste collected in the bed pan as it is being utilized by a male patient.

2. The invention in accordance with claim 1 wherein the fastening means includes a pair of opposing arms extending from the central support cup and a fastener on each of the arms for attaching the arm to a bed pan.

3. The invention in accordance with claim 2 wherein the fastener is an adhesive surface on the end portion of each arm.

4. The invention in accordance with claim 3 wherein a portion of each arm containing the adhesive is capable of being bent with respect to the remainder of the arm to facilitate mounting of the adhesive surface on a bed pan.

5. The invention in accordance with claim 1 wherein a substantially horizontal flap extends from a portion of the lip of the central support cup.

6. The invention in accordance with claim 1 wherein the central support cup has an open upper end.

7. The invention in accordance with claim 1 wherein the scrotum sac is of a plastic material.

8. The invention in accordance with claim 1 wherein the scrotum sac is integrally formed as part of a bed pan.

* * * * *